(12) United States Patent
Mosa et al.

(10) Patent No.: US 10,099,007 B2
(45) Date of Patent: Oct. 16, 2018

(54) DRESSING FOR USE WITH AN INFUSION KIT

(75) Inventors: Fatoona Mosa, York (GB); Simon Tyson, York (GB)

(73) Assignee: Smith & Nephew plc, York (GB)

( * ) Notice: Subject to any disclaimer, the term of this patent is extended or adjusted under 35 U.S.C. 154(b) by 1135 days.

(21) Appl. No.: 14/110,026

(22) PCT Filed: Apr. 3, 2012

(86) PCT No.: PCT/GB2012/000308
§ 371 (c)(1),
(2), (4) Date: Jan. 13, 2014

(87) PCT Pub. No.: WO2012/136954
PCT Pub. Date: Oct. 11, 2012

(65) Prior Publication Data
US 2014/0121638 A1    May 1, 2014

(30) Foreign Application Priority Data

Apr. 4, 2011  (GB) .................................. 1105626.4
Apr. 5, 2011  (GB) .................................. 1105715.5

(51) Int. Cl.
*A61M 5/158*    (2006.01)
*A61M 25/02*    (2006.01)
(Continued)

(52) U.S. Cl.
CPC ....... *A61M 5/158* (2013.01); *A61F 13/00085* (2013.01); *A61F 13/0259* (2013.01); *A61M 25/02* (2013.01); *A61M 2025/0273* (2013.01)

(58) Field of Classification Search
CPC .. A61M 2025/0273; A61M 2005/1586; A61M 5/158; A61M 25/02;
(Continued)

(56) References Cited

U.S. PATENT DOCUMENTS 4,275,721 A * 6/1981  Olson .................. A61M 5/158
128/DIG. 26
4,307,719 A * 12/1981  McParland ........... A61M 25/06
604/264
(Continued)

FOREIGN PATENT DOCUMENTS

DE    202007007634 U1    8/2007
EP         0051935 A2 *  5/1982  ........... A61F 13/023
(Continued)

OTHER PUBLICATIONS

Authorized officer Radim Sedy, International Search Report/Written Opinion in PCT/GB2012/000308 dated Jul. 17, 2012, 5 pages.
(Continued)

*Primary Examiner* — Nathan R Price
*Assistant Examiner* — Weng Lee
(74) *Attorney, Agent, or Firm* — Fish & Richardson P.C.

(57) ABSTRACT

A dressing, for use in securing an infusion set on a skin surface, the dressing consisting of a film having a skin contacting surface and a non-skin-contacting surface, the skin-contacting surface being provided with an adhesive; a releasable backing layer provided on the non-skin-contacting surface of the film; a releasable liner provided on the skin-contacting surface of the film layer and overlaying the adhesive wherein an aperture is provided having a first portion extending from an edge of the film, backing layer and liner opening into a second portion having a geometry which is identical or substantially similar to the geometry of the perimeter of the hub of an infusion set, and wherein at least one handle is provided between the film and the liner.

20 Claims, 3 Drawing Sheets

(51) Int. Cl.
*A61F 13/00* (2006.01)
*A61F 13/02* (2006.01)

(58) Field of Classification Search
CPC .. A61M 2025/0246; A61M 2025/1586; A61M 2025/0206; A61M 2025/0266; A61M 25/0245; A61F 13/00085; A61F 13/0259; A61F 13/0263; A61F 13/0266
See application file for complete search history.

(56) References Cited

U.S. PATENT DOCUMENTS

| | | | | |
|---|---|---|---|---|
| 4,490,141 A | * | 12/1984 | Lacko | A61M 25/02 128/879 |
| 4,614,183 A | * | 9/1986 | McCracken | A61F 13/023 128/846 |
| 4,941,882 A | * | 7/1990 | Ward | A61F 13/023 128/DIG. 26 |
| 5,352,211 A | | 10/1994 | Merskelly | |
| 5,709,651 A | * | 1/1998 | Ward | A61F 13/023 602/42 |
| 5,968,000 A | * | 10/1999 | Harrison | A61M 25/02 602/41 |
| 2002/0115954 A1 | * | 8/2002 | Worthley | A61F 13/0246 602/57 |

FOREIGN PATENT DOCUMENTS

| | | |
|---|---|---|
| EP | 117632 A2 | 9/1984 |
| WO | WO2007011596 A2 | 1/2007 |

OTHER PUBLICATIONS

Examination Report issued in Canadian Application No. 2,832,016 dated Jan. 12, 2018.

* cited by examiner

DRESSING FOR USE WITH AN INFUSION KIT

FIELD OF THE INVENTION

The invention relates to a dressing to secure an infusion kit, for example an insulin infusion sets, on the skin of a patient and methods for applying the dressing.

BACKGROUND TO THE INVENTION

Small, portable diabetic infusion sets deliver fast-acting insulin 24 hours a day, eliminating the need for injections. An example of a kit is illustrated in FIG. 1. The insulin is delivered from the pump via tubing at the end of which is a soft, flexible cannula. With the help of an insertion device, this cannula is placed under the skin and remains in place for several days. An adhesive dressing can be used to help hold the infusion set in place.

The current infusion sets have a non-woven adhesive pad extending about the hub. However, this mechanism may not be adequate for holding the infusion set in place during strenuous activity. Users frequently use adhesive film dressings to help provide additional fixation to infusion sets. With standard square dressings which cover the whole infusion set the dressing needs to be completely removed before the user can disconnect the pump from the infusion set. Infusion set IV3000 was designed to fit around the infusion set so that it provides additional fixation security but allows the user to connect and disconnect without removing the dressing.

SUMMARY OF THE INVENTION

According to a first aspect of the invention there is provided a dressing for use in securing an infusion set on a skin surface, said dressing comprising;
(i) a film having a skin-contacting surface and a non skin-contacting surface, the skin-contacting surface being provided with an adhesive;
(ii) a releasable backing layer provided on the non-skin contacting surface of the film;
(iii) a releasable liner provided on the skin contacting surface of the film layer and overlying the adhesive wherein an aperture is provided having a first portion extending from an edge of the film, backing layer and liner opening into a second portion having a geometry which is identical or substantially similar to the geometry of the perimeter of the hub of an infusion set, and wherein a pair of handles are provided between the film and the liner.

According to a second aspect of the invention there is provided a method of securing an infusion set to a skin surface of a subject said method comprising the steps of;
(i) providing an infusion set comprising a pump with a tube extending therefrom, the tube having a cannula at a distal end;
(ii) inserting the cannula into an infusion site on a subject;
(iii) providing a dressing as claimed in claim 1;
(iv) removing the releasable liner provided on the skin-contacting surface of the film layer to expose the adhesive on the skin-contacting surface of the film layer;
(v) positioning the dressing using the pair of handles such that the first portion of the aperture facilitates the passing of the dressing about the tube in situ and the second portion of the aperture locates around the hub;
(vi) removing the pair of handles
(vii) removing the backing layer.

For ease of application of the dressing, preferably the user will follow the temporal sequence of steps of securing the infusion set is as above and as illustrated in FIG. 3, although it is also envisaged that the sequence of steps (iv), (v), (vi) and (vii) may be interchangeable.

According to a third aspect of the invention there is provided a kit comprising an infusion set and at least one dressing according to the first aspect of the invention.

According to a fourth aspect of the invention there is provided the use of the dressing according to the first aspect of the invention in the retention of an infusion set on a skin surface.

According to a fifth aspect of the invention there is provided a dressing, a method or a kit as substantially herein before described with reference to the accompanying FIGS. 2 and 3.

In embodiments of the invention the infusion set is a diabetic infusion set. However it is also envisaged that the dressing could be used on other devices in which a tube/cannula requires retention to the skin, for example, glucose sensors.

Advantageously in some embodiments of the invention an edge of the backing layer extends over a corresponding edge of the film, to form a tab-like element, thereby facilitating the removal of the backing layer.

Following the application of the dressing, the film will overlay the upper surface of the non-woven adhesive pad extending about the hub. As the geometry of the second portion of the aperture is either identical or closely matches the geometry of the hub this minimises the area of the non-woven pad that is not covered by the film, which consequently minimises the potential for any water to permeate between the film layer and pad during, for example, showering. Any such permeation could compromise the safety of the dressings as it could facilitate microbial growth at or near to the infusion site.

DETAILED DESCRIPTION OF THE INVENTION

The invention will now be described with reference to the accompanying drawings in which.

Figure 1:
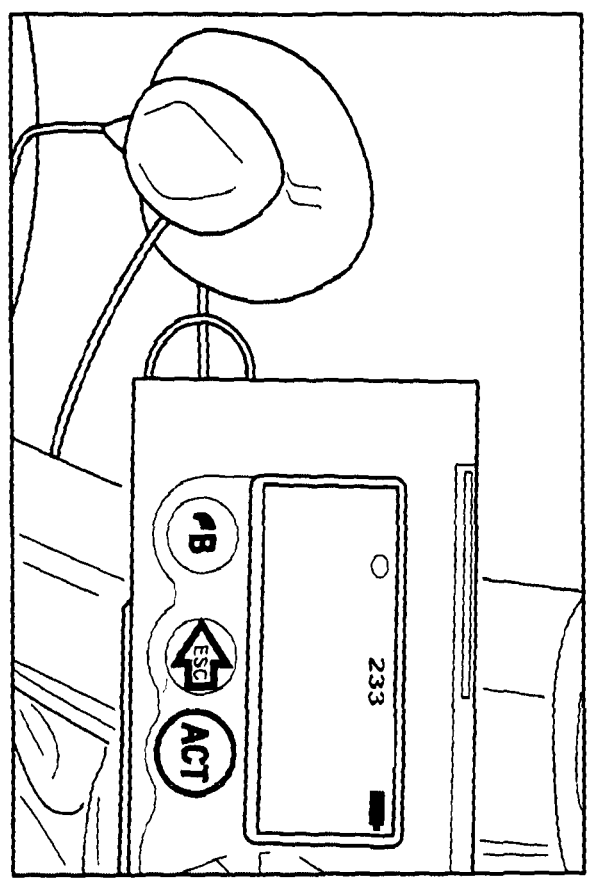
FIG. 1 shows an example of a diabetic infusion pump with an infusion set.
Figures 2A, 2B:
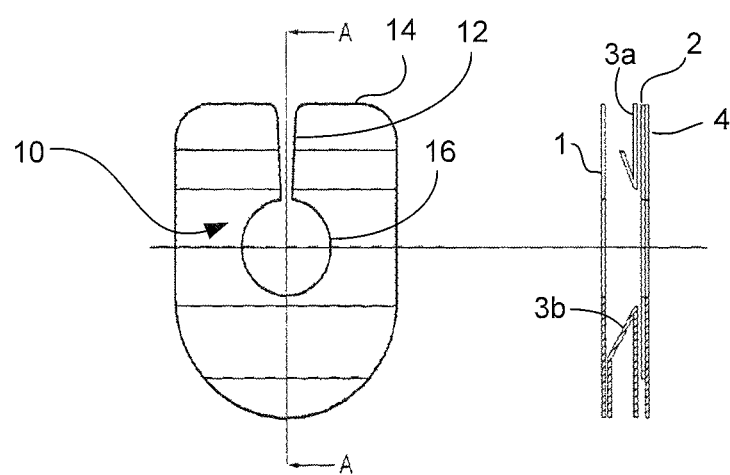
FIGS. 2A-2D show first and second embodiments of the dressing.
Figures 2C, 2D:
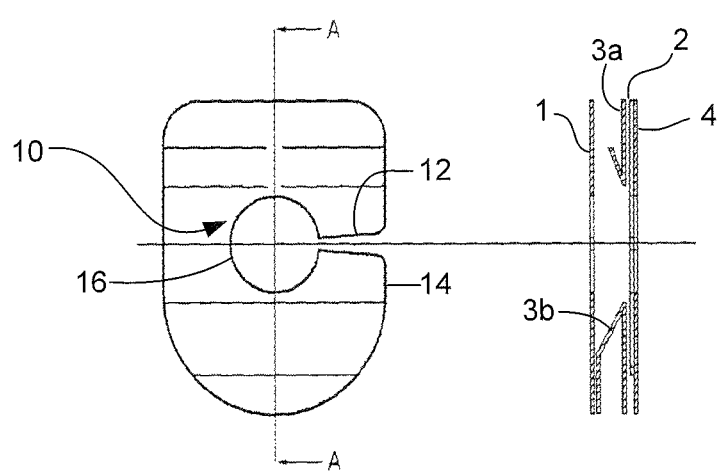
Figure 3:
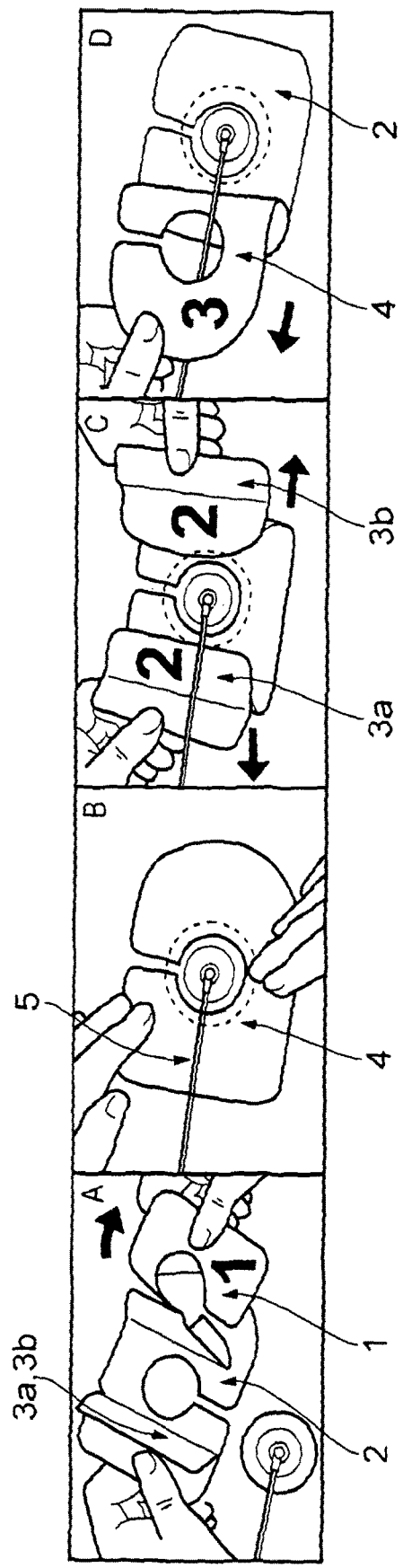
FIG. 3 illustrates a sequence of application of the dressing.

Panel A—The release liner (1) is removed to expose the adhesive on the lower surface of the film (2) and a pair of handles (3a;3b);

In specific embodiments of the invention the film (2) is polyurethane which is pattern spread on the skin-contacting surface with a pressure sensitive acrylic adhesive.

In specific embodiments of the invention the releasable liner (1) and the pair of releasable handles (3a;3b) are made of a coated/non-coated paper. The pair of releasable handles (3a;3b) are sandwiched between the film and the releasable liner and are located at or near opposing edges of the film. Each handle comprises or consists of a piece of folded-paper, designed such that when handling the dressing the users fingers can fit into the fold.

Panel B—The dressing with the backing layer (4) overlaying the non skin-contacting surface of the film (2) and also with the pair of handles (3a;3b) in place is positioned about the tubing (5).

In specific embodiments of the invention the releasable backing layer (4) is made of LDPE/HDPE. In order to facilitate removal of the backing layer, at least one of its edges extends over an edge of the film layer.

Panel C—The pair of handles (3a;3b) are removed from beneath the backing layer (4);

Panel D—The backing layer (4) is removed.

In specific embodiments of the invention an edge of the backing layer (4) extends beyond the corresponding edge of the underlying film which aids in the removal of the backing layer as this extending edge acts like a tab.

An aperture 10 is provided having a first portion 12 extending from an edge 14 of the film, backing layer and liner opening into a second portion 16 having a geometry which is identical or substantially similar to the geometry of the perimeter of the hub of the infusion set.

The invention claimed is:

1. A dressing, for use in securing an infusion set on a skin surface, said dressing comprising:
   (i) a film having a skin-contacting surface and a non-skin-contacting surface, the skin-contacting surface being provided with an adhesive;
   (ii) a releasable backing layer provided on the non-skin-contacting surface of the film;
   (iii) a releasable liner provided on the skin-contacting surface of the film layer and overlaying the adhesive, at least one of the liner and backing layer defining a most outer edge of the dressing extending along an entire perimeter of the dressing, wherein an aperture is provided having a first portion extending from the most outer edge, and the first portion opens into a second portion of the aperture having a geometry which is identical or substantially similar to a geometry of a perimeter of a hub of an infusion set, and wherein at least one handle is provided below the film and above the liner, the at least one handle being located entirely within the perimeter of the dressing and spaced entirely laterally from a circumference of the second portion of the aperture.

2. A dressing as claimed in claim 1 in which the at least one handle is a pair of handles that are provided between the film and liner.

3. A dressing as claimed in claim 1 in which the at least one handle is a plurality of handles.

4. A dressing as claimed in claim 1 in which the geometry of the second portion of the aperture is substantially circular or round.

5. A dressing as claimed in claim 1 in which the backing layer extends over a corresponding edge of the film.

6. A dressing as claimed in claim 1 in which the at least one handle, a pair of handles or a plurality of handles comprises of a folded material.

7. A dressing as claimed in claim 2 in which the pair of handles are located at or near opposing edges of the film.

8. A dressing as claimed in claim 1 in which the at least one handle is made of a coated/non-coated paper.

9. A method of securing an infusion set to a skin surface of a subject, said method comprising the steps of:
   (i) inserting a cannula of an infusion set into an infusion site on a subject, the infusion set comprising a pump with a tube extending therefrom, the tube having the cannula at a distal end, the infusion set having a hub with a perimeter;
   (ii) removing a releasable liner provided on a skin-contacting surface of a film layer of a dressing to expose an adhesive on the skin-contacting surface of the film layer, the dressing having the film layer having the skin-contacting surface and a non-skin-contacting surface, and a releasable backing layer provided on the non-skin-contacting surface of the film layer, at least one of the liner and backing layer defining a most outer edge of the dressing extending along an entire perimeter of the dressing, wherein an aperture is provided having a first portion extending from the most outer edge, the first portion opens into a second portion of the aperture having a geometry identical or substantially similar to a geometry of the perimeter of the hub of the infusion set, and wherein at least one handle is provided below the film layer and above the liner, the at least one handle being located entirely within the perimeter of the dressing;
   (iii) positioning the dressing using the at least one handle, such that the first portion of the aperture facilitates the passing of the dressing about the tube in situ and the second portion of the aperture locates around the hub, followed by;
   (iv) adhering the dressing to the skin around the hub so that the hub is exposed through the second portion of the aperture, followed by;
   (v) removing the at least one handle; and
   (vi) removing the backing layer.

10. The dressing as claimed in claim 1 in which the at least one handle is provided such that the liner can be removed followed by removal of the handle.

11. The method as claimed in claim 9 in which the step of removing the releasable liner occurs before the step of removing the at least one handle.

12. The dressing as claimed in claim 1 wherein the at least one handle is located entirely within the perimeters of the liner and the backing layer.

13. The dressing as claimed in claim 2 wherein the pair of handles are located entirely within the perimeter of the dressing.

14. The dressing as claimed in claim 13 wherein the pair of handles are located entirely within the perimeters of the liner and the backing layer.

15. The dressing as claimed in claim 1 wherein the liner extends to the perimeter of the dressing.

16. The dressing as claimed in claim 1 wherein the liner is flat.

17. The dressing as claimed in claim 1 wherein the at least one handle extends to the perimeter of the dressing.

18. The method as claimed in claim 9 wherein the liner extends to the perimeter of the dressing.

19. The method as claimed in claim 9 wherein the liner is flat.

20. The method as claimed in claim 9 wherein the at least one handle extends to the perimeter of the dressing.

* * * * *